United States Patent
Kanellos et al.

(10) Patent No.: US 6,815,535 B1
(45) Date of Patent: Nov. 9, 2004

(54) PURIFICATION OF FIBRINOGEN

(75) Inventors: Jerry Kanellos, Victoria (AU); Teresa Martinelli, Victoria (AU); Grace Demaria, Victoria (AU); Neil Goss, Victoria (AU)

(73) Assignee: CSL Limited, Victoria (AU)

( * ) Notice: Subject to any disclaimer, the term of this patent is extended or adjusted under 35 U.S.C. 154(b) by 0 days.

(21) Appl. No.: 09/600,911

(22) PCT Filed: Jan. 25, 1999

(86) PCT No.: PCT/AU99/00050
§ 371 (c)(1),
(2), (4) Date: Aug. 1, 2000

(87) PCT Pub. No.: WO99/37680
PCT Pub. Date: Jul. 29, 1999

(30) Foreign Application Priority Data

Jan. 23, 1998 (AU) .............................................. PP1481
Feb. 13, 1998 (AU) .............................................. PP1829

(51) Int. Cl.$^7$ .................................................. A23J 1/00
(52) U.S. Cl. ..................................................... 530/412
(58) Field of Search ................................ 530/412, 350, 530/383; 514/8, 12, 21; 435/6, 701

(56) References Cited

U.S. PATENT DOCUMENTS

| | | | | |
|---|---|---|---|---|
| 4,278,594 A | * | 7/1981 | Amrani ....................... | 530/383 |
| 4,341,764 A | | 7/1982 | Wallace et al. ............. | 424/101 |
| 4,789,733 A | * | 12/1988 | Winkelman .................. | 530/383 |
| 5,290,918 A | | 3/1994 | Bui-Khac | |
| 5,605,887 A | * | 2/1997 | Pines et al. .................... | 514/21 |
| 2002/0131970 A1 | * | 9/2002 | Altieri et al. | |

OTHER PUBLICATIONS

Mosesson, Biochimica ET Biophysica Acta, vol. 57, pp. 204–213, 1962.*

Menitove, et al.; "Evaluation of factor VIII–rich cryoprecipitate . . . from single–dono plasma units"; Transfusion (Philadelphia), 1987, 27(6), 491–5, 1987, Abstract XP002198065.

Smith, et al; "A heparin–precipitable fraction of human plasma . . . of the fraction"; J. Clin. Invest.; 1957, 36, 596–604, 1957, Abstract XP002198066.

Bukurestliev, et al; "Production of an enriched factor VIII reagent! . . . Faktor–VIII–Praparates"; Folia Haematologica Internationales Magazin Fur Klinische und Morphologische Blutforschung, 1976, 103 (5) 742–5; Abstract XP002198067.

Holm, et al; "Does qualitatively altered fibrinogen . . . fraction (HPF) in acute myocardial infraction (AMI)?"; Thromb. Res. (1984), 33(1), 9–18, 1984, Abstract XP002198068.

Palmer et al, "Development of aHeat–Treated Factor VII/ von Willebrand Factor . . . ," Thrombosis and Haemostasis, vol. 63, No. 3, pp. 392–402 (1990).

Tien et al, "Yields of Fibronectin by Heparin–Cold–Precipitation . . . ," Annals Academy of Medicine, vol. 19, No. 6 (1990).

Nanu et al, "Extraction & assay of fibronectin from stored plasma," Indian J. Med Res [B], vol. 94, pp. 80–82 (1991).

* cited by examiner

Primary Examiner—Karen Cochrane Carlson
Assistant Examiner—Sheridan Snedden
(74) Attorney, Agent, or Firm—Nixon & Vanderhye

(57) ABSTRACT

Method of obtaining a fibrinogen enriched preparation by (i) adding an effective amount of a sulphated polysaccharide (SPS) to a fibrinogen containing solution to form a fibrinogen containing precipitate and (ii) extracting fibrinogen from the fibrinogen containing precipitate from step (i) with a solution containing at least 0.1M salt to obtain a fibrinogen enriched preparation.

22 Claims, No Drawings

PURIFICATION OF FIBRINOGEN

FIELD OF THE INVENTION

The present invention relates primarily to a method of obtaining fibrinogen. The method of the present invention also enables the obtaining of fibronectin and Factor XIII.

BACKGROUND OF THE INVENTION

The isolation of human fibrinogen has traditionally been carried out by classical plasma fractionation methods. Fibrinogen is precipitated from plasma either with ethanol (Blomback and Blomback, 1956), ammonium sulphate (Takeda, 1996), β alanine/glycine (Jakobsen and Kieruif, 1976), polymers (polyethelene glycol) and low ionic strength solutions (Holm, 1985) with relative high yield and homogeneity.

Further purification of fibrinogen precipitates can be achieved by ion-exchange chromatography conditions (Stathakis, 1978) and affinity chromatography (Kuyas, 1990). Specific contaminants can be absorbed out for example fibronectin an immobilised gelatine and plasminogen an immobilised lysine (Vuento, 1979).

Over the past few decades the overall structure and function of the fibrinogen molecule has been elucidated. The completion of the amino acid sequence of human fibrinogen (Henschen and Lottspeich, 1977) and the assignment of disulphide bonds (Blomback et al. 1976, Douma et al. 1978) provided data that confirmed the pioneer observations of an extended multidomained molecule (Hah and Slayter, 1959). The cloning of the fibrinogen genes and the complete amino acid sequence of all three chains of human fibrinogen from the cDNA studies are in agreement with those reported earlier based on the conventional amino acid sequencing procedures (Chung et al. 1983).

Precipitation methods are widely used for the manufacture of commercial fibrinogen. Chromatographic methods are now being explored as an alternative or to improve the purity of fibrinogen concentrates.

Fibrinogen interacts with a number of physiologically important proteins (Doolittle, 1984) such a plasminogen, thrombin, fibronectin, certain strains of staphylococcal bacteria and platelets. A number of functional characteristics have been assigned to specific parts of the molecule including: the position of the fibrinopeptides released from the parent molecule by catalytic action of thrombin, fibrin covalent stabilisation donor and acceptor sites, carbohydrate clusters, polymerisation sites, calcium binding sites and the attachment sites for fibronectin, plasminogen, bacteria and platelets.

Human fibrinogen has a strong affinity for fibrin and this association has been exploited to affinity purify fibrinogen. Fibrin immobilised on Sepharose was used to isolate fibrinogen from human plasma (Matthias et al. 1975). Protein structure function studies have identified the peptide sequences in fibrin that have been shown to specifically bind to fibrinogen. Short peptides beginning with the sequence Gly-L-Pro-Arg have been shown to bind fibrinogen (Laudano and Doolittle, 1978). This sequence corresponds to the first three amino acids of the fibrin α-chain exposed by the thrombin catalysed release of the fibrinopeptide A in all vertebrate species. The addition of a second proline to this sequence was later shown to increase the affinity of the peptide Gly-Pro-Arg-Pro for fibrinogen almost ten-fold (Laudano and Doolittle, 1980). Based on this information, synthetic peptides corresponding to these sequences have also been shown to bind to fibrinogen (Gartner and Taylor, 1991).

SUMMARY OF THE INVENTION

The present invention relates to the large scale separation by precipitation of fibrinogen from other blood proteins in human blood plasma, cryoprecipitate, fraction 1 precipitate, other plasma fractions containing fibrinogen or fibrinogen containing culture media produced by recombinant DNA techniques and subsequent treatment of the heparin precipitate. The resultant fibrinogen-enriched preparation may be further purified to homogeneity utilising other precipitation methods, chromatographic steps such as ion-exchange chromatography, affinity chromatography size exclusion chromatography or ultrafiltration.

The present inventors have found that fibrinogen may be recovered from heparin precipitated paste, a by-product from the manufacturing process of Factor VIII (Antihaemophilic Factor, AHF). The heparin precipitate paste may be solubilised with salt containing solutions such as NaCl to provide a fibrinogen preparation of high specific activity. The method of this invention has been shown to be superior to other known isolation procedures in that fibrinogen may be obtained with relative high yield and homogeneity from a discard fraction of processed plasma.

Accordingly, the present invention consists in a method of obtaining a fibrinogen enriched preparation, the method including the following steps:

(i) adding an effective amount of a sulphated polysaccharide (SPS) to a fibrinogen containing solution to form a fibrinogen containing percipitate; and (ii) extracting fibrinogen from the fibrinogen containing percipitate from step (i) with a solution containing at least 0.1 M, and preferably at least 0.2M, salt to obtain a fibrinogen enriched preparation.

In a preferred embodiment of the present invention the solution includes at least one salt selected from the group consisting of chloride, phosphate and acetate salts, and more preferably includes NaCl. It is preferred that the NaCl is present at concentration of from about 0.1M to about 2.0M, preferably from about 0.2M to about 0.8M.

In a further preferred embodiment the solution includes ε-aminocaproic acid.

In another preferred embodiment the SPS is a heparinoid selected from the group consisting of mucopolysaccharide polysulphate, pentosan polysulphate, chondroitin sulphate, dextran sulphate and heparin and is preferably heparin.

The amount of SPS used can be readily determined, however, it is preferred that the SPS is added to the fibrinogen containing solution to provide a concentration of SPS of at least 0.15 mg/ml.

Where the fibrinogen is to be used therapeutically the fibrinogen will be subjected to a viral inactivation step(s). Such inactivation procedures are well known in the art and include heating and solvent detergent treatment.

The fibrinogen containing solution may be any of a number of such solutions well known to those skilled in the art such as plasma (including anti-coagulated plasma), plasma fractions (such as cryoprecipitate and solubilised fraction I) and fibrinogen-containing cell culture media arising from the production of fibrinogen by recombinant DNA techniques. It is, however, preferred that the fibrinogen containing solution is a blood plasma fraction, preferably cryoprecipitate.

The fibrinogen may be further purified from the fibrinogen enriched preparation using any of a range of techniques well known to those skilled in this area. For example, purifying the fibrinogen from the fibrinogen enriched preparation by either reprecipitating the fibrinogen with a protein precipitant in the presence of salts and/or amino acids or by chromatographic techniques such as ion exchange, affinity, hydrophobic or gel permeation chromatography or a combination of both techniques. For use the fibrinogen enriched preparation will typically be treated to remove SPS and/or plasminogen. This can be achieved using a number of methods well known in the art. Examples of known purification methods include those described in the following references, the disclosures of which are incorporated herein by reference:

"Affinity purification of human fibronectin on immobilized gelatine" Regnault V, Rivat C, & Stoltz; Journal of Chromatography, 432 (1988) 93–102

"Isolation of Fibronectin under Mild Conditions" Morgenthaler J, Baillod P & Friedli H; Vox Sang 47 (1984) 41–46

"Plasminogen: Purification from human plasma by affinity chromatography" Deutsch D & Mertz E; Science 170 (1970) 1095–1096

"A Pasteurised Concentrate of Human Plasma Factor XIII for Therapeutic Use" Winkelman L, Sims G, Haddon M, Evans D & Smith J; Thrombosis and Haemostasis 55(3) (1986) 402–405

"The Preparation of Human Fibrinogen Free of Plasminogen" Mosesson M; Biochim Biophys Acta 57 (1962) 204–213

U.S. Pat. No. 3,340,156

"Severely Heated Therapeutic Factor VIII Concentrate of High Specific Activity" Winkelman L, Owen n, Evans D, Evans H, Haddon M, Smith J, Prince P & Williams J; Vox Sang 57 (1989) 97–103

"Plasma Protein Fractionation" Heide K, Haupt H & Schwick H; in The Plasma Proteins, 2nd Edition Vol 3 (1977) Putnam F. (Ed)

Depending on the nature of the fibrinogen containing solution the fibrinogen enriched preparation may also contain fibronectin and Factor XIII. For example, if the fibrinogen containing solution is plasma or a plasma fraction the fibrinogen enriched preparation will also contain fibronectin and/or Factor XIII. If desired these proteins may also be further purified from the fibrinogen enriched preparation using known separation techniques.

Accordingly, the present invention also provides a method of obtaining a preparation enriched for fibronectin or Factor VIII, the method comprising extracting fibronectin or Factor VIII from the fibronectin enriched preparation obtained according to the method of the present invention in which the fibrinogen containing solution is a blood plasma fraction.

As will be recognised from the above description the present invention provides a method of purifying fibrinogen from blood plasma concentrates especially cryoprecipitate. The most commercially important of the plasma concentrates currently used are the blood plasma fraction commonly known as cryoprecipitate and purified concentrates prepared from cryoprecipitate. Conventionally, cryoprecipitate is defined as a precipitate rich in Factor VIII and fibrinogen and which is prepared from frozen freshly prepared human plasma by a low temperature plasma fractionation technique.

Typically deep frozen plasma is softened at temperatures below 5° C. and the Factor VIII rich cryoprecipitate is collected by centrifugation.

Cryoprecipitate prepared in this way has been used as a commercial source of Factor VIII and typically contained concentrated within it from 40 to 60% of the total amount of Factor VIII contained in the whole blood from which the plasma is derived. There have been numerous studies designed to improve the yield of Factor VIII from cryoprecipitate and to further purify it. The presence of high concentrations of fibrinogen and fibronectin in Factor VIII preparations is undesirable because they have been found to give rise to unacceptable losses of Factor VIII during some of the processing steps. Fibrinogen is of particular concern because it is normally present in much greater concentrations than fibronectin in blood plasma and cryoprecipitate and is usually more difficult to remove than fibronectin.

A method of preparing a Factor VIII containing preparation which includes the steps of precipitating fibrinogen and fibronectin from a buffered solution of a Factor VIII containing blood plasma fraction by the addition of a sulphated polysaccharide is disclosed by Winkleman (AU B55435/86) who described one method of purifying Factor VIII in which the fibrinogen is precipitated from a buffered solution of cryoprecipitate held at pH 6 to 8.

The heparin precipitate is removed from the Factor VIII containing supernatant and discarded. The present invention enables the purification of valuable proteins from this previous waste product.

DETAILED DESCRIPTION

In order that the nature of the present invention may be more clearly understood preferred forms thereof will now be described with reference to the following examples.

MATERIALS
BUFFERS
Tris Buffer
  50 mM Tris
  5 mM EDTA
  5 mM ε-aminocaproic acid
  0.8 M NaCl
  pH 7.3
Citrate Buffer
  20 mM Na-Citrate
  5 mM EDTA
  5 mM ε-aminocaproic acid
  0.8 M NaCl
  pH 7.3
Tris wash Buffer
  50 mM Tris
  5 mM EDTA
  5 mM ε-aminocaproic acid
  pH 7.3

Heparin paste is a by-product from the manufacture of AHF (High Purity). It is obtained from production and then stored in 100 g aliquots at −80° C.

METHOD
Buffer Optimisation Study

Heparin paste was thawed in a 37° C. water bath and allowed to equilibrate to room temperature for 30 minutes. Heparin paste (6 g) was added to 50 ml of the extraction buffer. This was incubated at room temperature for 30 minutes, stirring at a rate where no frothing occurs. The solubilised paste was centrifuged at 4,200 rpm for 10 minutes at 4° C. The mass of both the pellet and supernatant was determined and the pellet was discarded. The supernatant was aliquoted (5 ml) and then frozen at −80° C.

The initial extraction of fibrinogen from Heparin paste was performed using Tris buffer (50 mM Tris, 5 mM EDTA, 5 mM ε-aminocaproic acid, 0.8 M NaCl, pH 7.3)(CSL work book 0525 pp 28–47). In these experiments, buffer components and conditions were altered to optimise the extraction procedure. Variations on the Tris buffer included:

removing one component of the Tris buffer and keeping all others constant varying the pH of the Tris buffer, and varying the NaCl concentration of the Tris buffer.

Variations of buffer components and conditions of Citrate buffer (20 mM Na-Citrate, 5 mM EDTA, 5 mM ε-aminocaproic acid, 0.8 M NaCl, pH 7.3) were also examined for their ability to extract fibrinogen from Heparin paste.

Variations on the Citrate buffer included:

removing one component of the Citrate buffer and keeping all others constant varying the pH of the Citrate buffer varying the NaCl concentration of the Citrate buffer minus EDTA, and varying the Na-Citrate concentration of the Citrate buffer.

Water for Injection BP (WFI) and WFI with 0.8 M NaCl were also examined for their ability to extract fibrinogen from Heparin paste.

The ability of each buffer to extract fibrinogen from Heparin paste was determined by analysis of total clottable fibrinogen, total protein and factor XIII activity in the supernatant.

Heparin Paste Concentration Study

The maximum amount of Heparin paste able to be solubilised in a constant volume of Tris buffer was determined. Heparin paste (obtained from production and processed immediately) was weighed out (6 g, 22 g and 40 g) and added to 50 ml of the Tris wash buffer. This was incubated at room temperature for 30 minutes, stirring at a rate where no frothing occurs. The paste was then separated from the wash buffer and transferred to a beaker containing 50 ml of Tris (extraction) buffer. This was incubated at room temperature for 30 minutes, stirring at a rate where no frothing occurs. The solubilised paste was centrifuged at 4,200 rpm for 10 minutes at 4° C. The mass of both the pellet and supernatant was determined and the pellet was discarded. The supernatant was aliquoted (5 ml) and then frozen at −80° C.

The ability of Tris buffer (constant volume) to extract fibrinogen from different amounts of Heparin paste was determined by analysis of total clottable fibrinogen, total protein, factor XIII activity and total plasminogen in the supernatant.

RESULTS

BUFFER OPTIMISATION STUDY

Experiment 1:

Experiment 1 showed that solubilisation of Heparin paste using Tris buffer resulted in the extraction of 14.1 mg/ml protein, with 75% being clottable fibrinogen (Table 1).

Heparin paste was also solubilised by Tris buffer minus specific components. For these buffers, extracted protein ranged from 14.2 mg/ml to 16.5 mg/ml, with 52–83% clottable fibrinogen being recovered (Table 1). The greatest amount of clottable fibrinogen, 83%, was extracted by solubilising Heparin paste in Tris buffer minus EDTA. Only 52% of clottable fibrinogen was extracted by solubilising Heparin paste in Tris buffer minus ε-aminocaproic acid and 66% when Tris buffer minus Tris was used (Table 1).

TABLE 1

Fibrinogen extraction from Heparin paste using Tris buffer minus specific components.

| Buffer | Heparin Paste (g) | Supernatant (ml) | Pellet (g) | Protein mg/ml (total) | Fibrinogen mg/ml (total) % clottable |
|---|---|---|---|---|---|
| Tris buffer | 6.1 | 53.5 | 1.0 | 14.1 (754.4) | 10.6 (567.1) 75% |
| Tris buffer minus Tris | 6.1 | 54.2 | 1.1 | 14.2 (769.6) | 9.3 (504.1) 66% |
| Tris buffer minus EDTA | 6.3 | 53.3 | 1.3 | 16.5 (879.5) | 13.7 (730.2) 83% |
| Tris buffer minus ε-amino-caproic acid | 6.0 | 54.2 | 1.1 | 14.9 (807.6) | 7.7 (417.3) 52% |

Experiment 2:

Experiment 2 showed that solubilisation of Heparin paste by Tris buffer (pH 6.0 to pH 8.0) resulted in comparable extracted protein levels, 15.0 mg/ml (Tris buffer pH 7.5) to 17.3 mg/ml (Tris buffer, pH 7.0). The proportion of clottable fibrinogen ranged from 48% (Tris buffer pH 8.0) to 60% (Tris buffer pH 7.3) (Table 2).

TABLE 2

Fibrinogen extraction from Heparin paste using Tris buffer at various pH levels.

| Sample | Heparin paste (g) | Supernatant (ml) | Pellet (g) | Protein mg/ml (total) | Fibrinogen mg/ml (total) % clottable |
|---|---|---|---|---|---|
| pH 6.0 | 6.2 | 55.7 | 1.0 | 16.3 (907.9) | 9.2 (512.4) 56% |
| pH 6.5 | 6.3 | 54.9 | 1.1 | 16.3 (894.9) | 9.6 (527.0) 59% |
| pH 7.0 | 6.4 | 52.4 | 1.4 | 17.3 (906.5) | 9.1 (476.8) 53% |
| pH 7.3 | 6.0 | 53.2 | 1.4 | 15.9 (845.9) | 9.6 (510.7) 60% |
| pH 7.5 | 6.2 | 56.7 | 1.4 | 15.0 (850.5) | 8.6 (487.6) 57% |
| pH 8.0 | 6.3 | 52.7 | 1.2 | 16.7 (880.1) | 8.0 (421.6) 48% |

Experiment 3:

Table 3 shows data obtained when Tris buffer, with varying concentrations of NaCl (0.2 M–2 M), were used for the extraction of fibrinogen from Heparin paste. The absence of NaCl resulted in partial solubilisation of the Heparin paste (5.3 g Heparin paste unsolubilised). Consequently, low levels of both protein and fibrinogen were recovered: 1.9 mg/ml of protein extracted with only 11% being clottable fibrinogen. The amount of protein extracted using Tris buffer with NaCl, 0.2 M–2 M, was comparable. The greatest level of clottable fibrinogen was obtained when Tris buffer containing 0.6 M NaCl was used (8.4 mg/ml). The percentage of clottable fibrinogen decreased with increasing salt concentration (greater than 0.6 M NaCl).

TABLE 3

Fibrinogen extraction from Heparin paste using Tris buffer with various NaCl concentrations.

| Sample NaCl Concentration | Heparin paste (g) | Supernatant (ml) | Pellet (g) | Protein mg/ml (total) | Fibrinogen mg/ml (total) % clottable |
|---|---|---|---|---|---|
| 0.0 M | 6.0 | 49.1 | 5.3 | 1.9 (93.3) | 0.2 (9.82) 11% |
| 0.2 M | 6.1 | 53.3 | 1.4 | 14.9 (794.2) | 6.8 (362.4) 46% |
| 0.4 M | 6.1 | 55.1 | 1.1 | 15.8 (870.6) | 7.8 (429.8) 49% |
| 0.6 M | 6.0 | 54.2 | 0.9 | 15.6 (845.5) | 8.4 (455.3) 54% |
| 0.8 M | 12.1 (100 ml buffer) | 104.9 | 1.7 | 16.9 (1772.8) | 7.0 (734.3) 41% |
| 1.0 M | 6.1 | 54.8 | 1.5 | 14.1 (772.7) | 5.9 (323.3) 44% |
| 1.5 M | 6.0 | 57.2 | 1.3 | 15.5 (886.6) | 6.2 (354.6) 40% |
| 2.0 M | 6.0 | 55.1 | 1.7 | 15.7 (865.1) | 4.5 (248.0) 29% |

Experiment 4:

Experiment 4 examined the effect of Citrate buffer on the solubilisation of three batches of Heparin paste. The level of protein extracted from Heparin paste using Citrate buffer was 14.7 mg/ml, 14.0 mg/ml and 17.4 mg/ml (Tables 4a, 4b and 4c respectively). Of this protein, 91% (Table 4a), 65% (Table 4b) and 95% (Table 4c) was clottable fibrinogen. Analysis of Heparin paste solubilised using Citrate buffer for factor XIII showed 5.2 IU/ml, 9.5 IU/ml and 8.4 IU/ml (Tables 4a, 4b and 4c, respectively).

Heparin paste was also solubilised by Citrate buffer minus specific components. The removal of EDTA from Citrate buffer had no effect on extraction of protein, clottable fibrinogen and factor XIII from Heparin paste (14.6 mg/ml, 99% and 4.3 IU/ml respectively, Table 4a, 13.2 mg/ml, 113% and 6.3 IU/ml, respectively, Table 4b, 14.5 mg/ml, 106% and 4.2 IU/ml, respectively, Table 4c). The removal of ε-aminocaproic acid also showed no effect on protein, clottable fibrinogen and factor XIII from Heparin paste (14.6 mg/ml, 86% and 3.9 IU/ml respectively, Table 4a, 14.5 mg/ml, 65% and 8.0 IU/ml, respectively, Table 4b, 14.7 mg/ml, 72% and 7.8 IU/ml, respectively, Table 4c). However, Citrate buffer without NaCl was not able to solubilise the Heparin paste resulting in undetectable levels of protein and fibrinogen in the supernatant. The use of Na-Citrate alone was also unable to extract protein, factor XIII or fibrinogen, from the three Heparin paste batches (Tables 4a, 4b and 4c).

TABLE 4a

Fibrinogen extraction from Heparin paste using Citrate buffer minus specific components.

| Sample | Heparin Paste (g) | Supernatant (ml) | Pellet (g) | Protein mg/ml (total) | Fibrinogen mg/ml (total) % clottable | FXIII IU/ml (total) |
|---|---|---|---|---|---|---|
| Citrate buffer | 6.2 | 53.3 | 2.2 | 14.7 (783.5) | 13.4 (714.2) 91% | 5.2 (277.2) |
| Citrate buffer minus EDTA | 6.0 | 52.3 | 2.8 | 14.6 (763.6) | 14.5 (758.4) 99% | 4.3 (224.9) |
| Citrate buffer minus ε-aminocaproic acid | 5.2 | 53.0 | 1.6 | 14.6 (773.8) | 12.5 (662.5) 86% | 3.9 (206.7) |
| Citrate buffer minus NaCl | 6.2 | 48.1 | 5.1 | undetectable | undetectable | NA |
| 20 mM Na-Citrate | 6.1 | 46.0 | 7.3 | undetectable | undetectable | NA |

TABLE 4b

Fibrinogen extraction from Heparin paste using Citrate buffer minus specific components.

| Sample | Heparin Paste (g) | Supernatant (ml) | Pellet (g) | Protein mg/ml (total) | Fibrinogen mg/ml (total) % clottable | FXIII IU/ml (total) |
|---|---|---|---|---|---|---|
| Citrate buffer | 6.1 | 53.6 | 2.5 | 14.0 (750.4) | 9.1 (487.8) 65% | 9.5 (509.2) |
| Citrate buffer minus EDTA | 6.0 | 53.9 | 2.5 | 13.2 (711.5) | 14.9 (803.1) 113% | 6.3 (339.6) |
| Citrate buffer minus ε-aminocaproic acid | 6.1 | 53.4 | 2.4 | 14.5 (774.3) | 9.4 (502.0) 65% | 8.0 (427.2) |
| Citrate buffer minus NaCl | 6.1 | 48.1 | 7.2 | undetectable | undetectable | NA |
| 20 mM Na-Citrate | 6.0 | 46.9 | 6.5 | undetectable | undetectable | NA |

TABLE 4c

Fibrinogen extraction from Heparin paste using Citrate buffer minus specific components.

| Sample | Heparin Paste (g) | Supernatant (ml) | Pellet (g) | Protein mg/ml (total) | Fibrinogen mg/ml (total) % clottable | FXIII IU/ml (total) |
|---|---|---|---|---|---|---|
| Citrate buffer | 6.0 | 45.1 | 2.2 | 17.4 (784.7) | 16.5 (744.2) 95% | 8.4 (378.8) |

TABLE 4c-continued

Fibrinogen extraction from Heparin paste using Citrate buffer minus specific components.

| Sample | Heparin Paste (g) | Super-natant (ml) | Pellet (g) | Protein mg/ml (total) | Fibrinogen mg/ml (total) % clottable | FXIII IU/ml (total) |
|---|---|---|---|---|---|---|
| Citrate buffer minus EDTA | 6.1 | 53.2 | 1.9 | 14.5 (771.4) | 15.4 (819.3) 106% | 4.2 (223.4) |
| Citrate buffer minus ε-amino-caproic acid | 6.1 | 52.7 | 1.8 | 14.7 (774.7) | 10.5 (555.4) 72% | 7.8 (411.1) |
| Citrate buffer minus NaCl | 6.1 | 41.3 | 7.0 | undetect-able | undetect-able | NA |
| 20 mM Na-Citrate | 6.1 | 45.3 | 6.9 | undetect-able | undetect-able | NA |

Experiment 5:

The pH optimisation for the Citrate buffer involved testing a pH range for 5.0 to 9.0. For pH ranges 6.0 to 9.0, protein and clottable fibrinogen levels extracted were comparable (13.5 mg/ml to 14.2 mg/ml and 85% to 94%). However, at pH 5.0, only 6.0 mg/ml of protein was extracted with 20% clottable fibrinogen (Table 5).

TABLE 5

Fibrinogen extraction from Heparin paste using Citrate buffer at various pH levels.

| Sample NaCl Concentration | Heparin paste (g) | Supernatant (ml) | Pellet (g) | Protein mg/ml (total protein) | Fibrinogen mg/ml (total) % clottable |
|---|---|---|---|---|---|
| pH 5.0 | 6.1 | 51.9 | 3.8 | 6.0 (311.4) | 1.2 (62.3) 20% |
| pH 6.0 | 6.1 | 53.5 | 2.1 | 13.9 (743.7) | 13.1 (700.9) 94% |
| pH 7.0 | 6.1 | 54.9 | 2.1 | 14.2 (779.6) | 12.0 (658.8) 85% |
| pH 7.3 | 6.0 | 54.5 | 2.3 | 13.8 (752.1) | 12.4 (675.8) 90% |
| pH 8.0 | 6.1 | 54.1 | 2.1 | 13.6 (735.8) | 11.9 (643.8) 87% |
| pH 9.0 | 6.1 | 53.7 | 2.0 | 13.5 (725.0) | 11.9 (639.0) 88% |

Experiment 6:

Citrate buffer minus EDTA and containing a range of NaCl concentrations (0 M–1 M) was used in experiment 6. Two experiments were performed to test this range of concentrations. Results from this experiment showed that the solubility of Heparin paste increases with increasing NaCl concentration in the Citrate buffer minus EDTA (Table 6). Heparin paste was found to be only sparingly soluble in Citrate buffer minus EDTA with 0.05 M or less NaCl. This is seen by the extraction of only 0.2 mg/ml–0.4 mg/ml protein and 0.3 mg/ml–0.6mg/ml clottable fibrinogen. In two different experiments the presence of 0.1 M NaCl in the buffer showed a range of 4.2 mg/ml–11.0 mg/ml protein (86%–105% clottable fibrinogen) was extracted. This increased to 12.3 mg/ml–14.7 mg/ml protein (107%–119% clottable fibrinogen) when 0.2 M NaCl or greater is present. A constant level of extracted protein and clottable fibrinogen was demonstrated by addition of increasing concentrations of NaCl (0.4 M–1.0 M) to the Citrate buffer minus EDTA. These levels are comparable to the control, Citrate buffer minus EDTA containing 0.8 M NaCl. The levels of factor XIII ranged from undetected to approximately 3 IU/ml when 0 M–0.1 M NaCl was incorporated into the buffer. When NaCl (0.2 M–1 M) was added to the Citrate buffer minus EDTA, factor XIII levels remained constant. A maximum value of 7.8 IU/ml factor XIII was obtained when 0.4 M NaCl was added to the Citrate buffer minus EDTA.

TABLE 6

Fibrinogen extraction from Heparin paste using Citrate buffer minus EDTA with various NaCl concentrations.

| Sample | Heparin Paste (g) | Super-natant (ml) | Pellet (g) | Protein mg/ml (total) | Fibrinogen mg/ml (total) % clottable | FXIII IU/ml (total) |
|---|---|---|---|---|---|---|
| 0.0 M | 6.0 | 47.8 | 7.2 | 0.2 (9.6) | 0.3 (14.34) 149% | NA |
| 0.05 M | 6.0 | 47.9 | 7.3 | 0.4 (19.2) | 0.6 (28.7) 149% | NA |
| 0.1 M NaCl minus EDTA | 6.0 | 48.7 | 6.4 | 4.2 (204.5) | 3.6 (175.3) 86% | 3.0 (146.1) |
| | 6.0 | 51.6 | 3.3 | 11.0 (567.6) | 11.6 (598.6) 105% | 3.3 (170.3) |
| 0.15 M | 6.0 | 52.8 | 2.3 | 12.8 (675.8) | 14.3 (755.0) 115% | 3.2 (169.0) |
| 0.2 M NaCl minus EDTA | 6.1 | 53.0 | 2.7 | 12.3 (651.9) | 13.2 (699.6) 107% | 7.2 (381.6) |
| | 6.0 | 53.6 | 1.9 | 14.7 (787.9) | 17.5 (938.0) 119% | 3.1 (166.2) |
| 0.4 M NaCl minus EDTA | 6.0 | 52.8 | 3.1 | 13.8 (728.6) | 15.0 (792.0) 109% | 7.8 (411.8) |
| 0.6 M NaCl minus EDTA | 6.1 | 55.0 | 2.0 | 14.3 (786.5) | 14.5 (797.5) 101% | 4.8 (264.0) |
| 0.8 M NaCl (control) minus EDTA | 6.1 | 54.7 | 2.2 | 14.1 (771.3) | 14.1 (771.3)[b] 100% | 7.3 (399.3) |
| 1 M NaCl minus EDTA | 6.1 | 55.3 | 2.2 | 14.0 (774.2) | 12.5 (691.3) 89% | 6.1 (337.3) |

Experiment 7:

Table 7 details the levels of protein and clottable fibrinogen recovered by varying the levels of Na-Citrate in the Citrate buffer (Experiment 7). As the Na-Citrate concentration increased from 5 to 80 mM, there was a slight increase in the level of protein extracted (13.4 mg/ml minimum, 15.1 mg/ml maximum) (Table 7). The levels of clottable fibrinogen increased, from 79% to 107%, as the amount of Na-Citrate increased to 20 mM (Table 7). A decline in the amount of clottable fibrinogen was observed when 40 mM and 80 mM Na-Citrate was added to the buffer (85% and 74%, respectively) (Table 7).

TABLE 7

Fibrinogen extraction from Heparin paste using Citrate buffer with various levels of Na-Citrate.

| Sample | Heparin paste (g) | Supernatant (ml) | Pellet (g) | Protein mg/ml (total) | Fibrinogen mg/ml (total) % clottable |
|---|---|---|---|---|---|
| 5.0 mM | 5.6 | 54.3 | 1.9 | 13.4 (727.6) | 10.6 (575.6) 79% |
| 10.0 mM | 6.1 | 52.7 | 2.2 | 14.7 (774.7) | 13.1 (690.4) 89% |
| 15.0 mM | 6.3 | 54.9 | 1.9 | 14.8 (812.5) | 12.4 (680.8) 84% |
| 20.0 mM | 6.2 | 53.3 | 2.2 | 14.7 (783.5) | 15.7 (836.8) 107% |
| 40.0 mM | 6.1 | 53.4 | 2.0 | 15.0 (801.0) | 12.4 (678.2) 85% |
| 80.0 mM | 6.1 | 55.1 | 1.5 | 15.1 (832.0) | 11.2 (617.1) 74% |

Experiment 8:

Fibrinogen extraction was also performed using WFI at pH 7.3. Although the amount of total protein extracted was low, 3.3 mg/ml, all was shown to be clottable fibrinogen (106%) (Table 8). Higher levels of protein (10.1 mg/ml) were recovered when 0.8 M NaCl (dissolved in WFI) was used as the extraction buffer (Table 8). Of this protein, 84% was clottable fibrinogen.

TABLE 8

Fibrinogen extraction from Heparin paste using WFI.

| Sample | Heparin Paste (g) | Supernatant (ml) | Pellet (g) | Protein mg/ml (total) | Fibrinogen mg/ml (total) % clottable |
|---|---|---|---|---|---|
| WFI pH 7.3 | 6.1 | 56.2 | 1.6 | 3.3 (185.5) | 3.3 (185.5) 100% |
| WFI containing 0.8 M NaCl | 6.4 | 53.3 | 1.5 | 10.1 (538.3) | 8.5 (453.1) 84% |

Experiment 9

HEPARIN PASTE CONCENTRATION STUDY

The amount of Heparin paste that could be solubilised by a constant volume of Tris buffer pH 7.3 was determined. Total protein extracted from 6 g of Heparin paste with 50 ml Tris buffer ranged from 14.9 mg/ml to 17.9 mg/ml containing 55%–71% clottable fibrinogen. The amount of active factor XIII extracted from this amount of Heparin paste ranged between 4.5 IU/ml to 6.2 IU/ml. This amount of solubilised Heparin paste was found to contain 14.1 µg/ml to 16.6 µg/ml plasminogen (Table 9).

When the mass of Heparin paste was increased to 22 g, the amount of protein extracted was 38.6 mg/ml with 58% attributed to clottable fibrinogen. The amount of plasminogen and factor XIII extracted was 18.6 µg/ml and 26.0 IU/ml, respectively (Table 9).

When solubilising approximately 40 g of Heparin paste, the amount of protein extracted ranged between 48.0 mg/ml and 53.1 mg/ml (Table 9). Of this, 56% to 79% was clottable fibrinogen. The amount of active factor XIII extracted from this amount of Heparin paste ranged between 24.6 IU/ml to 27.5 IU/ml. This amount of solubilised Heparin paste was found to contain 21.5 µg/ml to 24.4 µg/ml plasminogen (Table 9).

TABLE 9

Fibrinogen extraction from 6 g. 22 g and 40 g Heparin paste using a constant volume of Tris buffer pH 7.3.

| Sample | Heparin Paste (g) | Supernatant (ml) | Pellet (g) | Protein mg/ml (total) | Fibrinogen mg/ml (total) % clottable | FXIII IU/ml (total) | Plasminogen µg/ml (total) |
|---|---|---|---|---|---|---|---|
| HepAS01-A1a | 6.0 | 55.1 | 1.1 | 14.9 (821.0) | 10.6 (584.1) 71% | 5.7 (314.1) | 15.2 (837.5) |
| H pAS02-A1b | 6.5 | 53.8 | 1.4 | 15.4 (828.5) | 10.3 (554.1) 67% | 5.1 (274.4) | 14.1 (758.6) |
| HepAS02-A1a | 6.0 | 55.3 | 1.4 | 17.3 (956.7) | 9.6 (530.9) 55% | 6.2 (342.9) | 15.5 (857.2) |
| HepAS02-A1b | 6.0 | 56.1 | 1.3 | 17.9 (1004.2) | 10.4 (583.4) 58% | 4.5 (252.5) | 16.6 (931.3) |
| HepAS02 A1HSB2 | 22.0 | 58.2 | 14.2 | 38.6 (2246.5) | 22.4 (1303.7) 58% | 26.0 (1513.2) | 18.6 (1082.5) |
| HepAS02 A1HSB1 | 41.0 | 84.6 | 6.3 | 53.1 (4492.3) | 30.0 (2538.0) 56% | 25.0 (2115.0) | 21.5 (1818.9) |

TABLE 9-continued

Fibrinogen extraction from 6 g. 22 g and 40 g Heparin paste using a constant volume of Tris buffer pH 7.3.

| Sample | Heparin Paste (g) | Supernatant (ml) | Pellet (g) | Protein mg/ml (total) | Fibrinogen mg/ml (total) % clottable | FXIII IU/ml (total) | Plasminogen µg/ml (total) |
|---|---|---|---|---|---|---|---|
| HepAS01 A1HSB | 40.4 | 76.6 | 13.4 | 52.0 (3983.2) | 40.8 (3125.3) 78% | 27.5 (2106.5) | 24.4 (1869.0) |
| H pAS01 A2HSB | 40.3 | 70.2 | 17.4 | 48.0 (3369.6) | 38.4 (2695.7) 79% | 24.6 (1726.9) | 24.3 (1705.9) |

Experiment 10

To demonstrate the applicability of the present invention to commercial application experiments were conducted using large quantities of heparin paste.

Results

Table 10 shows the results of the characterisation of fibrinogen extracted from heparin paste derived from the AHF(HP) process. This process involves dissolving cryoprecipitate in Tris buffer containing 0.8 mg/mL of heparin to form a heparin paste. Six batches of AHF(HP) heparin paste produced from plasma, ranging from 1733 kg to 2618 kg, were extracted using 20 mM Tri-sodium Citrate buffer containing 400 mM NaCl and 5 mM ε-aminocaproic acid. Total protein extracted ranged from 14.1 mg/mL–16.7 mg/mL of which 79%–85% was clottable protein. Levels of fibronectin and plasminogen averaged 3.9 mg/mL and 46.1 µg/mL, respectively.

Table 11 shows the results of the characterisation of fibrinogen extracted from heparin paste derived from the Biostate process using 20 mM Tri-sodium Citrate buffer containing 400 mM NaCl and 5 mM ε-aminocaproic acid. (The Biostate process involves dissolving cryoprecipitate in water including a low level of heparin and the adding further heparin to a concentration of about 1.0 mg/mL to obtain a heparin paste). The total mass of plasma used to produce this heparin paste ranged from 1556 kg–1635 kg. Total protein extracted ranged from 11.5 mg/mL–12.8 mg/mL of which 71%–85% was clottable protein. Levels of fibronectin and plasminogen averaged 2.75 mg/mL and 34.4 µg/mL, respectively.

Table 12 details the yield of fibrinogen obtainable from each kilogram of plasma. Purification of fibrinogen from heparin paste derived from the AHF(HP) process yields an average of 0.68 g per kg of plasma (range 0.62 g–0.79 g). Purification of fibrinogen from heparin paste derived from the Biostate process yields an average of 0.425 g per kg of plasma (range 0.4 g–0.45 g).

TABLE 10

Characterisation of solubilised heparin paste from cryoprecipitate extracted with Tris buffer

| Batch No. | Heparin paste mass (kg) | Vol. of SHP (L) | Total Protein mg/ml | Fibrinogen mg/mL | Clottable protein | Fibrinogen g/kg paste | Fibronectin mg/mL | Plasminogen µg/mL |
|---|---|---|---|---|---|---|---|---|
| 2 | 11.9 | 111.4 | 16.1 | 12.7 | 79 | 118.3 | 4.1 | 56.5 |
| 3 | 9.8 | 91.0 | 16.1 | 13.1 | 82 | 121.7 | 4.3 | 56.9 |
| 4 | 15.6 | 145.6 | 14.8 | 12.1 | 82 | 112.2 | 3.4 | 48.0 |
| 5 | 15.6 | 145.4 | 16.7 | 14.2 | 85 | 132.4 | 3.9 | 43.0 |
| 8 | 17.2 | 159.9 | 14.1 | 11.2 | 79 | 103.9 | 4.2 | 34.1 |
| 9 | 10.9 | 101.4 | 14.6 | 12.1 | 83 | 112.7 | 3.6 | 38.1 |

TABLE 11

Characterisation of solubilised heparin paste from cryoprecipitate extracted with water

| Batch No. | Heparin paste mass (kg) | Vol. of SHP (L) | Total Protein mg/ml | Fibrinogen mg/mL | Clottable protein | Fibrinogen g/kg paste | Fibronectin mg/mL | Plasminogen µg/mL |
|---|---|---|---|---|---|---|---|---|
| 6 | 7.8 | 72.6 | 12.8 | 9.1 | 71 | 84.4 | 3.1 | 35.5 |
| 7 | 7.85 | 73.0 | 11.5 | 9.5 | 82 | 88.2 | 2.4 | 33.3 |

TABLE 12

Yield of fibrinogen from plasma

| Batch No. | Mass of plasma (kg) | Fibrinogen in SHP | g fibrinogen/kg plasma |
| --- | --- | --- | --- |
| 2 | 2277 | 1359 | 0.62 |
| 3 | 1733 | 1192 | 0.69 |
| 4 | 2491 | 1762 | 0.71 |
| 5 | 2605 | 2065 | 0.79 |
| 8 | 2618 | 1791 | 0.68 |
| 9 | 1949 | 1227 | 0.63 |
| 6 | 1635 | 661 | 0.4 |
| 7 | 1556 | 693 | 0.45 |

Fibrinogen has been extracted from heparin paste that was derived from cryoprecipitate extracted in Tris buffer or in water. This process has been performed at a large scale (1.5–2.6 tonne of plasma). This preparation contains very high levels of fibrinogen with up to 90% clottable protein. In addition, the extracted material contains fibronectin, plasminogen and factor XIII.

As is demonstrated this method of extracting fibrinogen from heparin paste will be useful in the large scale manufacture of fibrinogen, fibronectin, plasminogen and factor XIII.

The first experiment aimed at determining which components of Tris buffer pH 7.3 (control buffer) were necessary for Heparin paste solubilisation and fibrinogen extraction. The removal of Tris, EDTA and ε-aminocaproic acid from the buffer did not affect Heparin paste solubilisation compared to the control. A difference however, was observed in the amount of clottable fibrinogen extracted by Tris buffer minus EDTA and Tris buffer minus ε-aminocaproic acid. Removal of EDTA from the buffer resulted in increased levels of extracted clottable fibrinogen compared to the control and other combinations of Tris buffer. This decrease in fibrinogen extracted by EDTA containing buffers may be due to assay inhibition caused by the EDTA.

Exclusion of ε-aminocaproic acid appeared to reduce clottable fibrinogen by 23% and may be an important component of the Heparin paste Tris extraction buffer.

Variation of the pH of the Tris buffer did not demonstrate any observable differences in Heparin solubilisation or fibrinogen extraction. The pH of the Tris buffer was thus maintained at pH 7.3.

The absence of salt such as NaCl from Tris buffer resulted in partial solubilisation of the Heparin paste. Consequently, low levels of clottable fibrinogen were recovered. The addition of 0.2 M NaCl to the buffer demonstrated an increase in clottable fibrinogen. Heparin paste solubilisation thus requires the presence of a salt such as NaCl for complete solubilisation and hence extraction of clottable fibrinogen. The amount of clottable fibrinogen was generally constant and comparable to the control (Tris buffer containing 0.8 M NaCl) for buffers containing 0.2 M–1.5 M NaCl. A sharp decline in clottable fibrinogen was observed for Tris buffer containing 2 M NaCl. Therefore, concentrations of NaCl greater than 1.5 M may affect the amount of clottable fibrinogen extracted from Heparin paste, or interfere with the assay.

Citrate buffer was also examined for its ability to solubilise and extract fibrinogen from Heparin paste compared to Tris buffer. Three different batches of Heparin paste were used for the Citrate buffer experiments. Citrate buffer pH 7.3 was able to extract greater than 90% clottable fibrinogen representing an increase in clottable fibrinogen, compared to Tris buffer (75%). Similar results to the Tris buffer component study were also seen when EDTA and ε-aminocaproic acid were removed from the Citrate extraction buffer. Again, increased clottable fibrinogen (approximately 100%) was observed when Citrate buffer minus EDTA was used to solubilise Heparin paste. This shows that EDTA is not necessary for fibrinogen extraction and that EDTA-containing buffers may interfere with the fibrinogen assay.

The use of Na-Citrate alone was ineffective in resolubilising the Heparin paste and therefore, protein and fibrinogen levels were undetectable. Variation of the Na-Citrate concentration (5 mM–80 mM) of the Citrate buffer showed 20 mM recovered the greatest amount of clottable fibrinogen. The amount of Na-Citrate in the Citrate buffer was thus maintained at this concentration.

Optimisation of Citrate buffer pH revealed that pH 6.0–9.0 did not affect the level of clottable fibrinogen extracted from Heparin paste. A difference was observed when pH 5.0 was used. The amount of protein extracted was less than half of that obtained from other pH levels tested and clottable fibrinogen fell to 21%, suggesting that fibrinogen activity was affected at this pH. At these pH levels, the Citrate buffer was able to extract approximately 90% clottable fibrinogen whereas Tris buffer extracted approximately 60%.

As observed in the Tris buffer studies, salt such as NaCl is also required in the Citrate buffer minus EDTA for solubilisation of Heparin paste and extraction of clottable fibrinogen. Complete removal of NaCl from the Citrate buffer minus EDTA resulted in decreased solubility of the Heparin paste. This decrease in solubility decreased protein and clottable fibrinogen extraction. Analysis of NaCl levels (0–0.2 M) showed very little protein was extracted from Heparin paste using Citrate buffer minus EDTA containing less than 0.1 M NaCl. Of this extracted protein, all was shown to be clottable fibrinogen. At least 0.15 M NaCl, in Citrate buffer minus EDTA pH 7.3, was required to extract greater levels of protein and thus fibrinogen from the Heparin paste. Increased NaCl, 0.1 M–0.2 M, resulted in increased protein and fibrinogen extraction, suggesting that at least 0.2 M NaCl is required for optimal solubilisation of Heparin paste by Citrate buffer minus EDTA. As the concentration of NaCl, within the Citrate buffer minus EDTA, increased from 0.15 M–0.6 M, so did the amount of protein extracted from the Heparin paste. When raised from 0.6 M to 1 M, no further increases in extracted protein were demonstrated. The amount of clottable fibrinogen extracted from the Heparin paste also increased with increasing NaCl concentrations (0.2 M–0.8 M). Levels of clottable fibrinogen extracted from Heparin paste decreased when concentrations of NaCl greater than 0.8 M were incorporated into the Citrate buffer minus EDTA. This suggests that the optimal concentration range of NaCl required for protein and clottable fibrinogen extraction is 0.2 M–0.8 M. This concentration of NaCl was also found to be necessary for the efficient solubilisation of Heparin paste by Tris buffer.

WFI, pH 7.3, with and without 0.8 M NaCl, was also examined for its ability to solubilise and extract fibrinogen from Heparin paste. This study demonstrated that Heparin paste was soluble in water and did not require a buffered solution for solubilisation. WFI, pH 7.3, extracted only low protein levels, however, all of this protein was shown to be fibrinogen. Again, the addition of greater than 0.2 M NaCl was necessary for increased extraction of protein and fibrinogen. WFI containing 0.8 M NaCl extracted comparable levels of fibrinogen compared to Tris buffer, pH 7.3, but lower levels compared to Citrate buffer.

The Heparin paste concentration study demonstrated that 6 g, 22 g, and 40 g Heparin paste were able to be solubilised by 50 mL Tris extraction buffer. Increasing levels of total protein were extracted from 6 g (902.6 mg), 22 g (2246.5 mg) and 40 g (3948.4 mg) of Heparin paste, respectively. If 902.6 mg of protein is extracted from 6 g of Heparin paste, then 3309.5 mg and 6017.3 mg of protein should be extracted from 22 g and 40 g of Heparin paste, respectively. Only 68% of the potential amount of protein is extracted when 22 g of Heparin paste is solubilised by Tris extraction buffer. Similarly, when 40 g of Heparin paste is solubilised, 66% of the potential amount of protein is extracted. Increasing levels of total clottable fibrinogen were extracted from 6 g (563.1 mg), 22 g (1303.7 mg) and 40 g (2786.3 mg) of Heparin paste, respectively. Again, if 6 g of Heparin paste produces a yield of 563.1 mg of clottable fibrinogen, then 2064.7 mg and 3754.0 mg of clottable fibrinogen should be extracted from 22 g and 40 g of Heparin paste, respectively. Only 63% of the potential amount of clottable fibrinogen is extracted when 22 g of Heparin paste is solubilised by Tris extraction buffer. Similarly, when 40 g of Heparin paste is solubilised, 74% of the potential amount of clottable fibrinogen is extracted. This suggests that although all concentrations of Heparin paste can be solubilised to some extent using a constant volume of Tris buffer, protein and clottable fibrinogen extraction are less efficient with increasing amounts of Heparin paste. This indicates that the optimum amount of Heparin paste required for efficient extraction of protein and clottable fibrinogen is 6 g in 50 ml of Tris extraction buffer.

Conclusion

The removal of Tris, EDTA and ε-aminocaproic acid from the Tris buffer did not affect Heparin paste solubilisation and protein extraction compared to the control (Tris buffer). However, removal of EDTA from Tris buffer demonstrated increased levels of clottable fibrinogen compared to the control and other combinations of Tris buffer. Increased levels of clottable fibrinogen was also observed when EDTA was removed from the Citrate buffer. This may be due to assay inhibition caused by inclusion of EDTA in these buffers. This also suggests that EDTA is not necessary for the extraction of fibrinogen from the Heparin paste.

The removal of ε-aminocaproic acid from both buffers appeared to reduce clottable fibrinogen and may therefore be an important component of the Heparin paste extraction buffers.

The inclusion of a salt such as NaCl was vital for the extraction of significant levels of fibrinogen and is therefore an essential component of the extraction solution. Tris buffer requires at least 0.2 M NaCl for maximum protein and clottable fibrinogen recovery. Like Tris buffer, it was demonstrated that the inclusion of NaCl in Citrate buffer and WFI was necessary for fibrinogen extraction. Citrate buffer requires at least 0.2 M NaCl for maximum protein and clottable fibrinogen recovery.

Variation of pH of the Tris buffer, demonstrated that all pH levels tested (6.0–9.0) were able to extract similar levels of fibrinogen compared to the control (pH 7.3). Variation of pH of the Citrate buffer demonstrated that pH 5.0 decreased extracted fibrinogen levels.

The amount of protein extracted by Tris buffer and Citrate buffer was comparable. However, Citrate buffer pH 7.3 was able to extract greater levels of clottable fibrinogen than Tris buffer. Since all other buffer components were the same, the presence of Na-Citrate (in place of Tris) in the Citrate buffer was able to stabilise fibrinogen to a greater extent than Tris. The optimal Na-Citrate concentration for the Citrate buffer is 20 mM. Na-Citrate at this concentration does not give the highest protein recovery but gives the greatest recovery of clottable fibrinogen. The average recovery of clottable fibrinogen is approximately 55% and approximately 100% for the Tris and Citrate buffers respectively. This emphasises the potential of the Citrate buffer for future extraction of fibrinogen from Heparin paste.

The disclosure of all references referred to herein are included herein by cross reference Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Blomback and Blomback (1956). *Ark Kemi*. 10:415–43.
2. Takeda, (1966). *J. Clin. Investigation*, 45:103–111.
3. Jakobsen and Kieruif, (1973). *Thrombosis Research*, 3:145–159
4. Holm at al (1985). *Thrombosis Research*, 37:165–176
5. Stathakis et al (1978). *Thrombosis Research*, 13:467–475
6. Kuyas, Haeberli, Walder and Straub, (1990). *Thrombosis & Haemostasis*, 64(3):439–444
7. Vuento et al (1979), *Biochemistry J*, 183:331–337
8. Henschen and Lottspeich, (1977). *Physiological Chemistry*, 358:935–938
9. Blomback, Hogg, Gardlund, Hessel and Kudryk, (1978). *Thrombosis Research*, 8(supp2):329–346
10. Bouma, Takagi and Doolittle, (1978). *Thrombosis Research*, 13:557–562
11. Hah and Slayter (1959). *J Biophys. Biochem. Cytol*. 5:11–15
12. Chung, Chan and Davies, (1983). *Biochemistry*, 22:3250–3256
13. Doolittle (1984). *Ann. Rev. Biochemistry*, 53:195–229
14. Matthias, Hocke and Lasch, (1975). *Thrombosis Research*, 7:861–870
15. Laudano and Doolittle, (1978). *Proc. Nat. Acad. Sci.* (*USA*)., 75:3085
16. Laudano and Doolittle, (1980). *Biochemistry*, 19:1013–1019
17. Gartner and Taylor, (1991). *PSEBM*, 198:649–655.

What is claimed is:

1. A method of obtaining a fibrinogen enriched preparation, the method comprising the following steps:
   (i) adding an effective amount of a sulphated polysaccharide (SPS) to a fibrinogen containing solution to form a precipitate containing fibrinogen; and
   (ii) extracting fibrinogen from the precipitate containing fibrinogen from step (i) with a solution containing at least 0.1M salt to obtain a fibrinogen enriched preparation.

2. A method as claimed in claim 1 in which the fibrinogen containing solution is a blood plasma fraction.

3. A method as claimed in claim 1 in which the solution comprises at least one salt selected from the group consisting of chloride, phosphate and acetate salts.

4. A method as claimed in claim 3 in which the solution comprises NaCl.

5. A method as claimed in claim 4 in which the NaCl is present at a concentration of from about 0.1M to about 2.0M.

6. A method as claimed in claim 1 in which the solution includes ε-aminocaproic acid.

7. A method as claimed in claim 1 in which the SPS is a heparinoid selected from the group consisting of mucopolysaccharide polysulphate, pentosan polysulphate, chondroitin sulphate, dextran sulphate and heparin.

8. A method as claimed in claim 1 in which the SPS is heparin.

9. A method as claimed in claim 1 in which the SPS is added to the fibrinogen containing solution to provide a concentration of SPS of at least 0.15 mg/ml.

10. A method as claimed in claim 1 in which the method further comprises the step of treating the fibrinogen enriched preparation to remove SPS or plasminogen.

11. A method as claimed in claim 1 in which the method further comprises the step of subjecting the fibrinogen enriched preparation to a viral inactivation step.

12. A method as claimed in claim 11 in which the viral inactivation step comprises heating or solvent detergent treatment.

13. A method as claimed in claim 1 in which the fibrinogen is further purified from the fibrinogen enriched preparation by ion exchange chromatography, affinity chromatography, hydrophobic or gel permeation chromatography or a combination thereof.

14. A method of obtaining a preparation enriched for fibronectin or Factor VIII, the method comprising the following steps:
   (i) adding an effective amount of a sulphated polysaccharide (SPS) to a fibrinogen containing solution to form a precipitate containing fibrinogen;
   (ii) extracting fibrinogen from the precipitate containing fibrinogen from step (i) with a solution containing at least 0.1M salt to obtain a fibrinogen enriched preparation;
   (iii) extracting fibronectin or Factor VIII from the fibrinogen enriched preparation obtained in step (ii).

15. A method as claimed in claim 1 in which the fibrinogen containing solution is a cryoprecipitate.

16. A method as claimed in claim 4 in which the NaCl is present at a concentration of from about 0.2M to about 0.8M.

17. A method as claimed in claim 1 in which the method further comprises the step of treating the fibrinogen enriched preparation to remove SPS and plasminogen.

18. A method as claimed in claim 11 in which the viral inactivation step comprises heating and solvent detergent treatment.

19. A method as claimed in claim 14 in which, in step (i), the fibrinogen containing solution is a cryoprecipitate.

20. A method as claimed in claim 14 in which, in step (ii), the solution contains at least 0.2M salt.

21. A method as claimed in claim 14 in which, in step (i), the fibrinogen containing solution is a blood plasma fraction.

22. A method as claimed in claim 1 in which, in step (ii), the solution contains at least 0.2M salt.

* * * * *